(12) United States Patent
LeBoeuf et al.

(10) Patent No.: US 11,617,545 B2
(45) Date of Patent: *Apr. 4, 2023

(54) METHODS AND SYSTEMS FOR ADAPTABLE PRESENTATION OF SENSOR DATA

(71) Applicant: Valencell, Inc., Raleigh, NC (US)

(72) Inventors: Steven Francis LeBoeuf, Raleigh, NC (US); Tushar Dilip Tank, Raleigh, NC (US); William M. Richey, Durham, NC (US); Michael Edward Aumer, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 41 days.

This patent is subject to a terminal disclaimer.

(21) Appl. No.: 17/394,565

(22) Filed: Aug. 5, 2021

(65) Prior Publication Data

US 2021/0393210 A1 Dec. 23, 2021

Related U.S. Application Data

(63) Continuation of application No. 16/734,498, filed on Jan. 6, 2020, now Pat. No. 11,109,809, which is a
(Continued)

(51) Int. Cl.
*G06T 11/20* (2006.01)
*A61B 5/00* (2006.01)
(Continued)

(52) U.S. Cl.
CPC .......... *A61B 5/7221* (2013.01); *A61B 5/0002* (2013.01); *A61B 5/022* (2013.01);
(Continued)

(58) Field of Classification Search
CPC ...... G06T 11/206; G06T 11/20; G06F 3/0481; G06F 17/246; H04L 41/22
(Continued)

(56) References Cited

U.S. PATENT DOCUMENTS

| 8,251,903 B2 | 8/2012 | Leboeuf et al. |
| 8,647,270 B2 | 2/2014 | Leboeuf et al. |

(Continued)

OTHER PUBLICATIONS

"Communication with Supplementary European Search Report",, EP Application No. 16873888.8, dated Sep. 20, 2018, 8 pp.
(Continued)

*Primary Examiner* — Gordon G Liu
(74) *Attorney, Agent, or Firm* — Myers Bigel, P.A.

(57) ABSTRACT

Systems and methods for presenting sensor data are provided and include collecting physiological data and meta data from a subject via a sensor system, wherein the sensor system comprises a sensor element, a signal processor, and memory in communication with the signal processor. The subject meta data is processed by the signal processor to determine metric features, the metric features are processed by the signal processor to determine a subject-specific metric statistic for the subject, and the physiological data is processed by the signal processor to generate a sensor metric. The sensor metric is then presented for display via a display.

33 Claims, 8 Drawing Sheets

Related U.S. Application Data continuation-in-part of application No. 16/563,105, filed on Sep. 6, 2019, now Pat. No. 10,765,374, which is a continuation of application No. 16/060,178, filed as application No. PCT/US2016/065742 on Dec. 9, 2016, now Pat. No. 10,441,224.

(60) Provisional application No. 62/266,196, filed on Dec. 11, 2015.

(51) Int. Cl.

| | | |
|---|---|---|
| *G16H 40/67* | (2018.01) | |
| *A61B 5/08* | (2006.01) | |
| *A61B 5/022* | (2006.01) | |
| *A61B 5/021* | (2006.01) | |
| *A61B 5/1455* | (2006.01) | |
| *G16H 50/20* | (2018.01) | |
| *A61B 5/145* | (2006.01) | |
| *A61B 5/024* | (2006.01) | |
| *G16H 50/30* | (2018.01) | |

(52) U.S. Cl.
CPC ........ *A61B 5/02108* (2013.01); *A61B 5/0816* (2013.01); *A61B 5/14551* (2013.01); *A61B 5/7282* (2013.01); *A61B 5/742* (2013.01); *G16H 40/67* (2018.01); *A61B 5/02405* (2013.01); *A61B 5/02416* (2013.01); *A61B 5/145* (2013.01); *A61B 2560/0242* (2013.01); *G16H 50/20* (2018.01); *G16H 50/30* (2018.01)

(58) Field of Classification Search
USPC ........................................................ 345/440
See application file for complete search history.

(56) References Cited

U.S. PATENT DOCUMENTS

| | | | |
|---|---|---|---|
| 8,700,111 | B2 | 4/2014 | Leboeuf et al. |
| 8,998,815 | B2 | 4/2015 | Venkatraman et al. |
| 2007/0270671 | A1 | 11/2007 | Gal |
| 2008/0133699 | A1 | 6/2008 | Craw et al. |
| 2008/0146892 | A1 | 6/2008 | Leboeuf et al. |
| 2008/0292151 | A1* | 11/2008 | Kurtz ................... A61B 5/442 382/128 |
| 2010/0177100 | A1 | 7/2010 | Carnes et al. |
| 2010/0249549 | A1 | 9/2010 | Baker et al. |
| 2010/0317420 | A1 | 12/2010 | Hoffberg |
| 2013/0192599 | A1 | 8/2013 | Nakai et al. |
| 2013/0231947 | A1 | 9/2013 | Shusterman |
| 2014/0135588 | A1* | 5/2014 | Al-Ali ................... G16H 40/63 600/300 |
| 2015/0031965 | A1 | 1/2015 | Visvanathan et al. |
| 2015/0099949 | A1 | 4/2015 | Wallace |
| 2015/0148694 | A1* | 5/2015 | Baruch ................ G16H 50/20 600/500 |
| 2015/0324692 | A1* | 11/2015 | Ritchey ............... A61B 5/1114 348/36 |
| 2016/0029964 | A1 | 2/2016 | Leboeuf et al. |
| 2016/0094899 | A1 | 3/2016 | Aumer et al. |
| 2016/0120433 | A1 | 5/2016 | Hughes et al. |
| 2016/0213317 | A1* | 7/2016 | Richardson ......... A61B 5/7278 |
| 2018/0360386 | A1 | 12/2018 | Leboeuf et al. |

OTHER PUBLICATIONS

"International Preliminary Report on Patentability", International Application No. PCT/US2016/065742, dated Mar. 5, 2018, 6 pp.

"International Search Report and Written Opinion of the International Searching Authority", International Application No. PCT/US2016/065742, dated Mar. 20, 2017, 13 pp.

"International Search Report and Written Opinion of the International Searching Authority, International Application No. PCT/US2020/012500, dated Mar. 18, 20, 11 pp."

Marc Peter Deisenroth , et al., "(2019). 'Density Estimation with Gaussian Mixture Models'. To be published in "Mathematics for Machine Learning" [Preprint]. Available at: https://mml-book.com. pp. 348-369".

\* cited by examiner

METHODS AND SYSTEMS FOR ADAPTABLE PRESENTATION OF SENSOR DATA

RELATED APPLICATIONS

This application is a continuation application of pending U.S. patent application Ser. No. 16/734,498, filed Jan.6, 2020, which is a continuation-in-part application of U.S. patent application Ser. No. 16/563,105, filed Sep. 6, 2019, now U.S. Pat. No. 10,765,374, which itself is a continuation application of U.S. patent application Ser. No. 16/060,178, filed Jun. 7, 2018, now U.S. Pat. No. 10,441,224, which itself is a 35 U.S.C. § 371 national stage application of PCT Application No. PCT/US2016/065742, filed on Dec. 9, 2016, which itself claims the benefit of and priority to U.S. Provisional Patent Application No. 62/266,196 filed Dec. 11, 2015, the disclosures of which are incorporated herein by reference as if set forth in their entireties. The above-referenced PCT International Application was published in the English language as International Publication No. WO 2017/100519 A1 on Jun. 15, 2017.

FIELD OF THE INVENTION

The present invention relates generally to monitoring devices and methods, more particularly, to monitoring devices and methods for measuring physiological information.

BACKGROUND OF THE INVENTION

FIG. 1 illustrates a conventional way of displaying biometric information 10 from a biometric sensor via a display 11 of a mobile electronic device 12, such as a smartphone, that is in communication with the biometric sensor. The biometric sensor that generates the data displayed in FIG. 1 is a blood pressure sensor that sends blood pressure information 12 and heart rate information 14 to an application (or "mobile app") running on the mobile electronic device for display. However, currently there is no mechanism by which a person can judge the accuracy of the displayed sensor information 10.

For example, if the mobile app connects with a first blood pressure sensor on one day and then connects with a second, different blood pressure sensor the another day, the person may get the same blood pressure readings from each blood pressure sensor. However, each blood pressure sensor may have a different accuracy, precision and probability distribution. For example, the first blood pressure sensor may have a standard deviation (σ) of 6 and the second blood pressure sensor may have a standard deviation (σ) of 9. Thus, even if the readings of both blood pressure sensors are the same, the person may not be able to trust the readings of the second sensor as much as those of the first sensor. To complicate matters further, the difference in accuracy or precision between the first and second blood pressure sensors may further depend on not just the sensor differences themselves, but also on static (or quasi-static) biometric data from the person being monitored, such as age, ethnicity, height, skin tone, weight, gender, medication usage, body mass index (BMI), health status, etc.

Moreover, when a mobile app is used to make a medical assessment or to plan an intervention or therapy, such as recommending a medical screening or suggesting blood pressure medication, there may be no good way to assess the probability of false alarms. Because the precision of each sensor may be different, the false positives, false negatives, true positives and true negatives in making a health assessment (such as a hypertension assessment, cardiovascular assessment, or the like) may be different for each sensor.

Thus, there is increased concern in the medical community as standards for wireless sensors, such as BLE (Bluetooth Low energy) standards, enable any biometric sensor to send biometric information because currently all sensors are mistakenly presumed to have equal statistical characteristics when making a medical assessment via a mobile application.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a method of presenting data from a sensor that is monitoring a subject and/or an environment in a vicinity of the subject includes displaying a sensor metric o simultaneously with sensor performance information via a display of an electronic device, such as a smartphone or other client device, that is in communication with the sensor. Exemplary sensor performance information includes information about the accuracy of the sensor and/or sensor measurement statistics. In some embodiments, the sensor performance information may be displayed as at least one probability distribution curve with the sensor data. The sensor performance information may be obtained from the sensor, from data storage, and/or from another source.

According to some embodiments of the present invention, a method of presenting physiological information via a display of an electronic device, such as a smartphone or other client device, includes receiving sensor data at the electronic device from a physiological sensor in communication with the electronic device, and then displaying the sensor data simultaneously with sensor performance information via the display. Exemplary physiological sensors include, but are not limited to PPG (photoplethysmography) sensors, blood pressure sensors, etc. The physiological sensor may be in wireless communication with the electronic device in some embodiments.

Exemplary sensor performance information includes information about the accuracy of the physiological sensor and/or sensor measurement statistics. In some embodiments, the sensor performance information may be displayed as at least one probability distribution curve with the sensor data. The sensor performance information may be obtained from the physiological sensor, from data storage, and/or from another source.

According to other embodiments of the present invention, a system includes a sensor configured to sense physiological information from a subject, and a signal processor configured to process signals from the sensor into a serial data stream of physiological information and sensor performance information. An electronic device having a display is configured to receive the serial data stream and display the physiological information simultaneously with the sensor performance information via the display. Exemplary sensor performance information includes information about the accuracy of the physiological sensor and/or sensor measurement statistics. In some embodiments, the signal processor is configured to process signals from the sensor into a serial data stream of physiological information, sensor performance information and sensor measurement statistics.

The electronic device may be a mobile communication device, such as a smartphone, and may be configured to receive the serial data stream from the physiological sensor wirelessly. In some embodiments the sensor performance information may be displayed as at least one probability distribution curve with the sensor data.

According to other embodiments of the present invention, a system includes a sensor configured to sense environmental information and a signal processor configured to process signals from the sensor into a serial data stream of environmental information and sensor performance information. An electronic device having a display, such as a smartphone or other portable device, is configured to receive the serial data stream and display the environmental information simultaneously with the sensor performance information via the display.

According to other embodiments of the present invention, a method of producing subject-specific metric statistics includes collecting physiological data and meta data from a subject via a sensor system, wherein the sensor system includes at least one sensor element, at least one signal processor, and memory in communication with the at least one signal processor. The collected data is processed by the at least one signal processor to determine a plurality of metric features from the collected data. The plurality of metric features are processed by the at least one signal processor to generate at least one subject-specific metric statistic and at least one sensor metric, and the at least one subject-specific metric statistic and the at least one sensor metric are displayed on a display, such as a display associated with a client device, e.g., a mobile communication device, etc.

The meta data from the subject may include one or more of the following: subject age, subject weight, subject height, subject gender, subject ethnicity. Collecting the meta data from the subject may include receiving the meta data as input from the subject or a third party. Collecting the meta data from the subject may also include determining the meta data from the physiological data.

In some embodiments, the at least one sensor element is a PPG sensor, the physiological data includes PPG data, and the at least one sensor metric comprises blood pressure.

In some embodiments, processing the plurality of metric features via the at least one signal processor to generate at least one subject-specific metric statistic comprises utilizing one or more data clustering techniques to generate a plurality of metric feature clusters. Exemplary data clustering techniques may include, but are not limited to, k-means and Gaussian mixture models.

In some embodiments, processing the plurality of metric features to generate at least one subject-specific metric statistic includes processing the plurality of metric features based on a desired metric statistic.

According to other embodiments of the present invention, a method of producing subject-specific metric statistics includes collecting physiological data and meta data from a subject via a sensor system, wherein the sensor system includes at least one sensor element, at least one signal processor, and memory in communication with the at least one signal processor. The collected data is processed via the at least one signal processor to determine a plurality of metric features from the collected meta data. The plurality of meta data metric features are processed via the at least one signal processor to generate at least one subject-specific metric statistic and to determine if the plurality of meta data metric features are associated with a desired metric statistic. The at least one subject-specific metric statistic and at least one sensor metric are displayed via a display, such as a display associated with a client device, e.g., a mobile communication device, etc.

The meta data from the subject may include one or more of the following: subject age, subject weight, subject height, subject gender, subject ethnicity. Collecting the meta data from the subject may include receiving the meta data as input from the subject or a third party. Collecting the meta data from the subject may include determining the meta data from the physiological data.

In some embodiments, the at least one sensor element is a PPG sensor, the physiological data includes PPG data, and the at least one sensor metric includes blood pressure.

In some embodiments, processing the plurality of meta data metric features to generate at least one subject-specific metric statistic and to determine if the plurality of meta data metric features are associated with a desired metric statistic includes utilizing one or more data clustering techniques to generate a plurality of metric feature clusters. Exemplary data clustering techniques may include, but are not limited to, k-means and Gaussian mixture models.

According to other embodiments of the present invention, a system includes at least one sensor configured to sense physiological data from a subject and receive subject meta data, and at least one signal processor. The at least one signal processor is configured to collect the physiological data and the meta data, process the collected data to determine a plurality of metric features from the collected data, process the plurality of metric features to generate at least one subject-specific metric statistic and at least one sensor metric, and display the at least one subject-specific metric statistic and the at least one sensor metric via a display. In some embodiments, the at least one signal processor is further configured to utilize one or more data clustering techniques to generate a plurality of metric feature clusters. Exemplary data clustering techniques may include, but are not limited to, k-means and Gaussian mixture models. In some embodiments, the at least one sensor is a PPG sensor, the physiological data includes PPG data, and the at least one sensor metric comprises blood pressure.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

DETAILED DESCRIPTION

Figure 1:
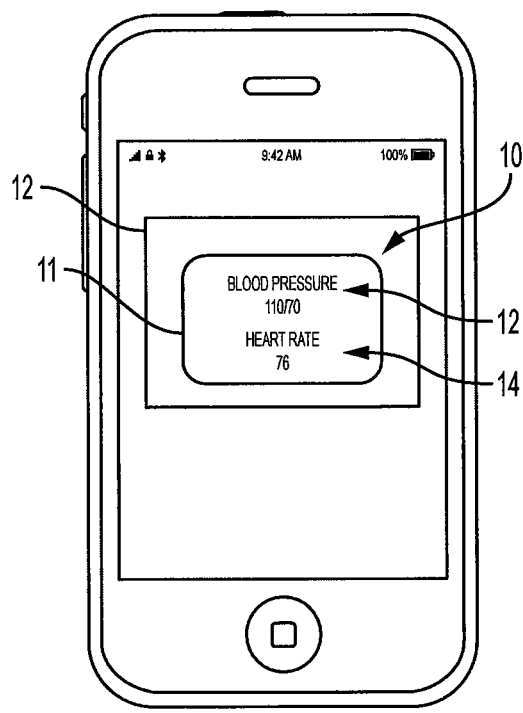
FIG. 1 illustrates a conventional display of biometric information to a person via a display of a mobile electronic device, such as a smartphone.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

The term "about", as used herein with respect to a value or number, means that the value or number can vary by +/− twenty percent (20%).

The term "remote", as used herein, does not necessarily mean that a remote device is a wireless device or that it is a long distance away from a device in communication therewith. Rather, the term "remote" is intended to reference a device or system that is distinct from another device or system or that is not substantially reliant on another device or system for core functionality. For example, a computer wired to a wearable device may be considered a remote device, as the two devices are distinct and/or not substantially reliant on each other for core functionality. Notwithstanding the foregoing, any wireless device (such as a portable device, for example) or system (such as a remote database for example) is considered remote to any other wireless device or system.

The terms "respiration rate" and "breathing rate", as used herein, are interchangeable.

The terms "heart rate" and "pulse rate", as used herein, are interchangeable.

The terms "sensor", "sensing element", and "sensor module", as used herein, are interchangeable and refer to a sensor element or group of sensor elements that may be utilized to sense information, such as information (e.g., physiological information, body motion, etc.) from the body of a subject and/or environmental information in a vicinity of the subject. A sensor/sensing element/sensor module may comprise one or more of the following: a detector element, an emitter element, a processing element, optics, mechanical support, supporting circuitry, and the like. Both a single sensor element and a collection of sensor elements may be considered a sensor, a sensing element, or a sensor module. A sensor/sensing element/sensor module may be configured to both sense information and process that information into one or more metrics.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature.

The term "body" refers to the body of a subject (human or animal) that may wear or otherwise be attached to a monitoring device or sensor, according to embodiments of the present invention.

As used herein, the term "processor" broadly refers to a signal processing circuit or computing system, or processing or computing method, which may be localized and/or distributed. For example, a localized signal processing circuit may comprise one or more signal processing circuits or processing methods localized to a general location, such as to an activity monitoring device. Examples of such devices may comprise, but are not limited to, an earpiece, a headpiece, a finger clip, a toe clip, a limb band (such as an arm band or leg band), an ankle band, a wrist band, a nose band, a sensor patch, apparel (clothing) or the like. Examples of a distributed processing circuit include "the cloud," the internet, a remote database, a remote processor computer, a plurality of remote processing circuits or computers in communication with each other, etc., or processing methods distributed among one or more of these elements. The difference between distributed and localized processing circuits is that a distributed processing circuit may include delocalized elements, whereas a localized processing circuit may work independently of a distributed processing system. Microprocessors, microcontrollers, or digital signal processing circuits represent a few non-limiting examples of signal processing circuits that may be found in a localized and/or distributed system.

The terms "mobile application", "mobile app" and "app", as used herein, are interchangeable and refer to a software program that can run on a computing apparatus, such as a mobile phone, digital computer, smartphone, database, cloud server, processor, wearable device, or the like.

The term "health", as used herein, is broadly construed to relate to the physiological status of an organism or of a physiological element or process of an organism. For example, cardiovascular health may refer to the overall condition of the cardiovascular system, and a cardiovascular health assessment may refer to an estimate of blood pressure, $VO_2$ max, cardiac efficiency, heart rate recovery, arterial blockage, arrhythmia, atrial fibrillation, or the like. A "fitness" assessment is a subset of a health assessment, where the fitness assessment refers to how one's health affects one's performance at an activity. For example, a $VO_2$ max test can be used to provide a health assessment of one's mortality or a fitness assessment of one's ability to utilize oxygen during an exercise.

The term "blood pressure", as used herein, refers to a measurement or estimate of the pressure associated with blood flow of a person.

The term "limits of agreement" (LOA), as used herein, refers to the limits of agreement between a sensor and a benchmark, typically using Bland-Altman formalism. For example, 95% LOA refers to a range of $\pm 1.96*\sigma$ about the mean difference between a sensor and a benchmark, where $\sigma$=the standard deviation of the sensor with respect to the benchmark. Approximately 95% of all data points collected by a sensor will fall between $\pm 1.96*\sigma$ of this mean difference. Thus a heart rate sensor estimate of 100 BPM (beats per minute), where the heart rate sensor is characterized by a $\sigma$=3 BPM and a mean difference of zero (all with respect to a benchmark), would indicate that the true heart rate could be between approximately 106 and 94 BPM, with approximately 95% certainty or higher.

The term "metric" generally refers to a measurement or measurement system of a property, and a "sensor metric" refers to a measurement or measurement system associated with a sensor. The metric may comprise an identifier for a type of measurement, a value of the measurement, and/or a diagnosis (i.e., an assessment) based on the measurement. For example, a metric may comprise "blood pressure", with a value of "120/80", and/or a diagnosis (assessment) of "normal".

The term "metric integrity", as used herein, refers to information relating how well a sensor, or a processor associated with a sensor, is able to dynamically track (in real time) the real value of a metric, based on prior statistical analysis of the sensor against a known benchmark. For example, the signal-to-noise (S/N) ratio of a signal can be analyzed by a processor and/or circuit and this information can be placed into a serial data stream, along with other sensor information, such that a mobile app can determine whether the sensor readings are truly tracking a metric, with metric integrity changing dynamically in real-time. In some embodiments of the present invention, metric integrity information may comprise numerical information on the "confidence" that the sensor readings are correct, wherein a higher confidence reading implies a higher confidence that the sensor is generating physiologically correct information as opposed to unwanted noise information (such as unwanted motion-, electrical-, or environmental-artifacts). An example of a system and method for generating S/N ratios for metric integrity (or signal "confidence") in a wearable PPG sensor module is presented in U.S. Patent Application Publication No. 2016/0094899, which is incorporated herein by reference in its entirety.

The term "metric statistic", as used herein, refers to static or quasi-static statistical information relating to the statistically validated performance of a sensor in a controlled benchmark study against a known benchmark sensor configured to sense the same metric. Examples of metric statistics may include, but are not limited to: standard deviation ($\sigma$), limits of agreement (LOA), $R^2$ coefficient, variance, % error, receiver-operating characteristic (ROC) curve information, and the like. As a specific example, blood pressure sensor data output may include information on the LOA with a known benchmark, for example: LOA=$\pm 10$ mmHg. While both metric integrity and metric statistics are based on statistical information, metric statistics are typically static or quasi-static and do not change during measurements, whereas metric integrity may change continuously with changing noise conditions in real-time. In the case where a sensor is configured to generate a diagnosis, such as a binary yes/no diagnosis of a health condition, rather than generating a metric value from a broad range of possible values, the metric statistics for that sensor may be better-described by diagnostic sensitivity/specificity analysis, with estimates for sensor accuracy, false positives, false negatives, true positives, true negatives, F1, markedness, informedness, false negative rate, false positive rate, Mathew's Correlation Coefficient, and the like. Thus, the metric statistics presented in a data stream may comprise information about the diagnostic sensitivity/selectivity characteristics. It should be noted that the metric statistic may be subject-specific, such that metric statistic for one subject may be different than that of another. In such case, additional subject information (such as subject meta data) may be required in order to generate the subject-specific metric statistic for the desired metric. Additionally, a subject-specific metric statistic may be different than the desired metric statistic—for example, the estimated accuracy of a metric for one subject may be less than the desired (i.e., targeted) accuracy of the metric generally across a large population. In such case, the reported metric statistic provided for the subject (the subject-specific metric statistic) may be a qualifier, such as "not suitable for targeted accuracy".

The term "sensor performance information", as used herein, refers to information about at least one functional characteristic of a sensor, configured to provide sensed information that can be used to generate a metric, such as a physiological, environmental, or physical activity metric. Examples of functional characteristics of a sensor include, but are not limited to, a metric statistic and/or metric integrity associated with the sensor.

The term "metric feature", as used herein, refers to a feature of input data that is functionally related to the estimation (or prediction) of a metric. A metric feature is generated by processing input data, such as sensor input data. For example, a machine learning model may learn a transfer function between a set of metric features and a metric, so that the metric features for a subject may then be used to predict the metric for the subject. As a specific example, a machine learning model may learn the relationship between subject metric features and subject blood pressure. In this specific example, the input data may comprise PPG, inertial sensor data, and subject meta data (such as subject height, weight, body-mass-index, age, gender, ethnicity, skin tone, medication usage, and the like). Metric features may then be generated by processing the input data. (In this particular example, the metric features for subject meta data may simply be processed as the meta data value itself.) When these metric features are then input into the algorithm developed by the machine learning model, a blood pressure metric may be generated.

Metric features for PPG waveforms may comprise an array of features about the waveforms, such as: RR-interval (i.e., beat-to-beat interval) features, rising slope(s), falling slope(s), integral of the waveform(s), spectral features of the waveforms, features generated by mathematical transforms of the waveforms (such as wavelet transforms, Fourier transforms, the Teager-Kaiser energy operator, chirplet transforms, noiselet transforms, and the like), waveform amplitude(s), waveform skews, auto-correlational features, and the like. As a specific example, the integral of PPG waveforms (collected via a PPG sensor on a subject) may be directly related to the blood flow volume of the subject, such that the "metric feature" of the "waveform integral" may be used by a model to predict the "metric" of blood flow volume.

The term "client device", as used herein, refers to a device that is separated by function and/or physical location from the sensor device, but is in wired or wireless communication with the sensor device. In some embodiments, the client device may be an integrated part of the sensor system (e.g., 90, FIG. 8) itself. In this case, the client device may comprise software and hardware (such as, but not limited to, software on a microprocessor) for receiving sensor data information. In addition, the client device may comprise software and hardware for presenting information (either visually, audibly, haptically, or the like) to someone or something.

It should be noted that the terms "confidence" and "signal quality" may often be used interchangeably herein. However, there are some slight differences between these two terms. Whereas "signal quality" relates primarily to the signal-to-noise ratio of a sensor reading, "confidence" relates primarily to an assessment based on "signal quality". For example, a high signal quality of a given threshold value may correspond with a 100% confidence threshold, such that sensor readings or sensor biometrics associated with signal qualities higher than the threshold value may be assumed to be accurate with a probability of 100%. The higher the signal quality, the higher one can trust a sensed metric, and thus the higher the metric integrity.

Figure 2:
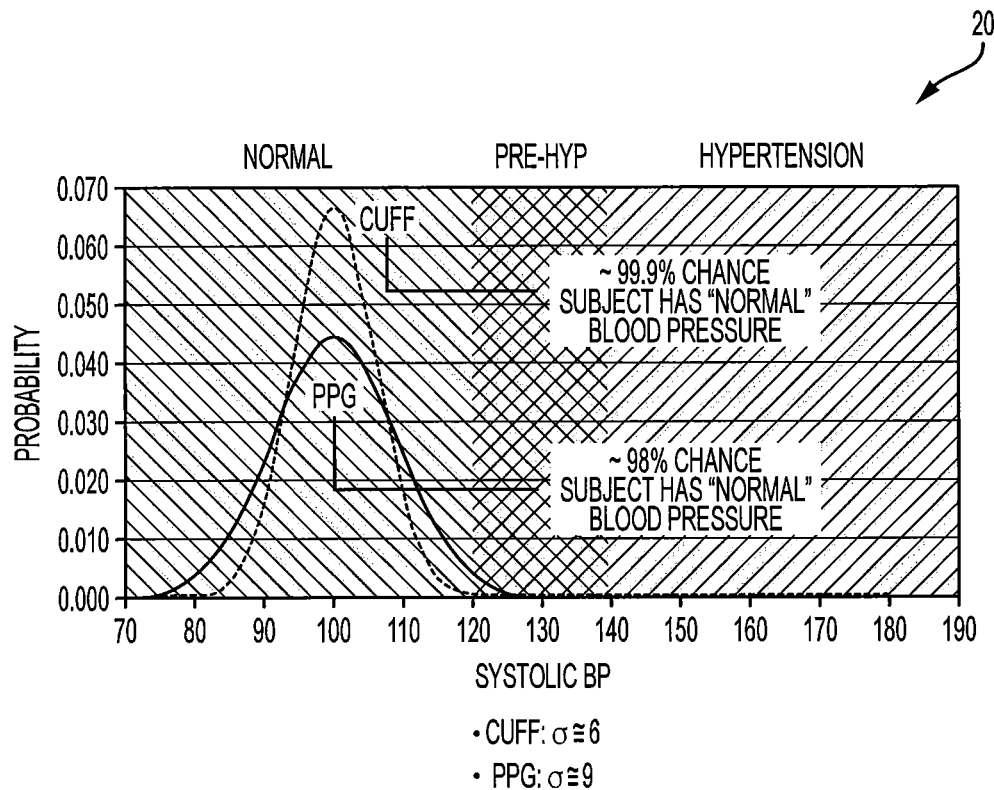
FIGS. 2 and 3 are probability plots for systolic and diastolic blood pressure sensors, respectively, and that can be displayed via a display of a mobile electronic device.
Figure 3:
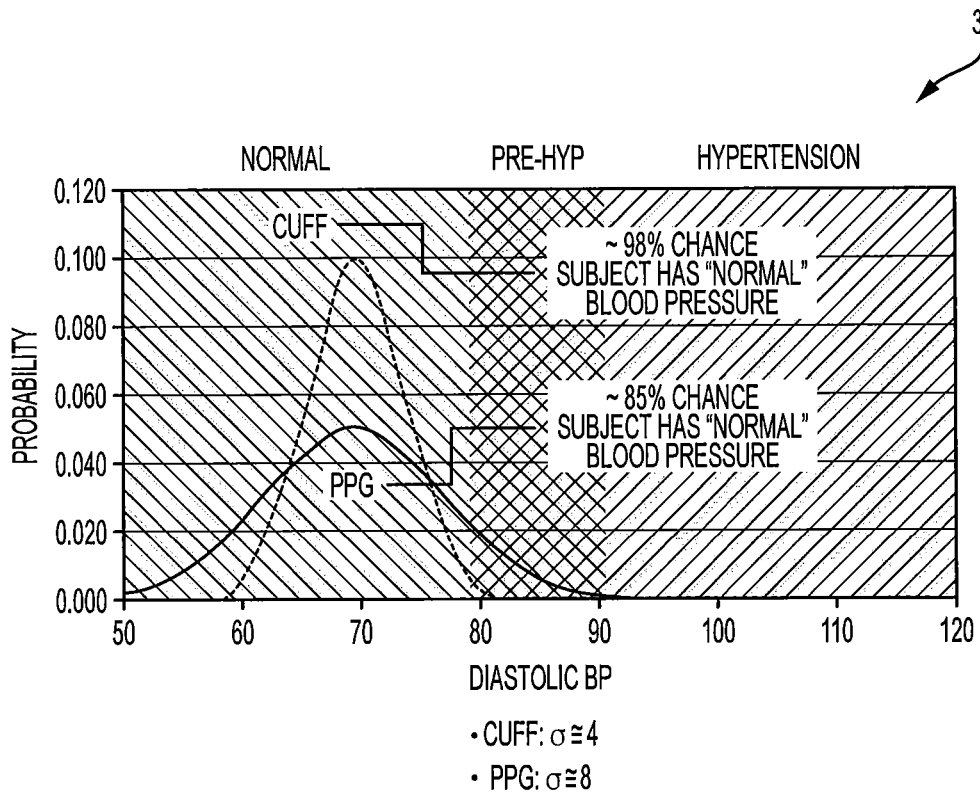

FIGS. 2 and 3 illustrate probability plots 20, 30 for systolic and diastolic blood pressure sensors, respectively. Two types of sensor probability distributions are shown for each plot: 1) PPG (photoplethysmography-based blood pressure sensor), and 2) cuff (cuff-based blood pressure sensor). The PPG-based blood pressure sensor has a broader probability distribution (higher standard deviation $\sigma$) than the cuff-based sensor. For example, if a person tested their blood pressure several times with both the PPG sensor and the cuff sensor, the mean blood pressures may be about the same, such as 100 mmHg, as illustrated in FIG. 2. However, the dispersion of readings over time may be broader for the PPG sensor, i.e., the variance ($\sigma^2$) of the Gaussian distribution may be higher for the PPG sensor. The 95% limits of agreement (LOA) for the PPG sensor would be $\pm 1.96 * \sigma_{PPG} \cong \pm 18$ mmHg when estimating systolic blood pressure, whereas the 95% LOA for the cuff would only be $\pm 1.96 * \sigma_{cuff} \cong 12$ mmHg. Thus, for the PPG sensor associated with FIG. 2, a random systolic blood pressure reading of 100 mmHg on the PPG sensor means there is a reasonable chance that the true systolic blood pressure is as high as 118 mmHg and as low as 82 mmHg. In contrast, the dispersion of possibilities for the cuff sensor is much lower. For example, as illustrated, true systolic blood pressure may be as high as 112 mmHg and as low as 88 mmHg. FIG. 3 presents similar information for diastolic readings from the same PPG sensor and blood pressure cuff sensor of FIG. 2, but with different calculations for the 95% LOA due to different values of $\sigma$ between the systolic and diastolic measurements.

Conventional mobile applications presenting data from a PPG sensor and/or a cuff sensor are not configured to present dispersion information to a user. For example, if a wireless (i.e. Bluetooth, WiFi, Zigbee, ANT+, etc.) PPG sensor and cuff sensor were both sending a diastolic reading of 70 mmHg to a mobile application (such as a smartphone or mobile device application), then the user may not be able to ascertain how well they can trust that measurement, or how many measurements they should make in order to arrive at the same average blood pressure measurement with each sensor. In contrast, embodiments of the present invention provide a meaningful way of presenting dispersion information to a user or someone monitoring the user (such as a medical practitioner). As such, embodiments of the present invention facilitate providing medical assessments (such as a hypertension assessment or the like) in context with false positives, false negatives, true positives, and true negatives. As such embodiments of the present invention are advantageous in that they may help improve the efficiency of medical triage and may help prevent the over- or under-prescribing of medications when a subject is using a mobile application for medical assessments or treatments.

Figure 4:
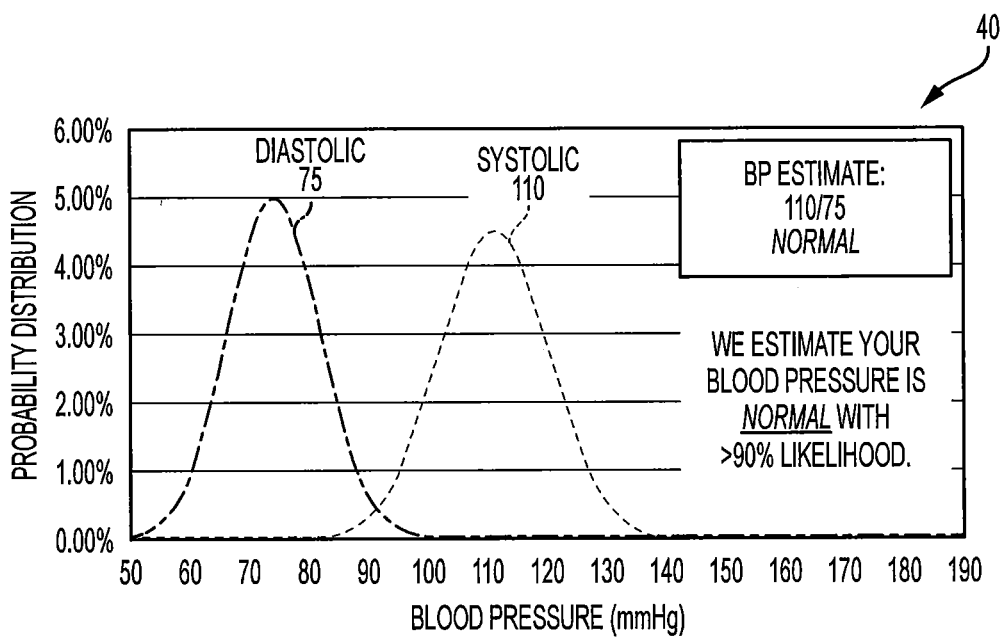
FIGS. 4-6 illustrate the presentation of biometric information and information about the integrity of the biometric information to a user, for example via a display of a mobile electronic device according to some embodiments of the present invention.

FIG. 4 illustrates a presentation 40 of biometric information from a physiological sensor (in this case blood pressure sensor), according to some embodiments of the present invention. The presentation 40 may be via a display of a mobile electronic device, for example, such as display 98 of client device 96 in FIG. 8. The presentation 40 allows the user and/or someone monitoring the user to assess the accuracy or urgency of the biometric assessment, e.g., a health assessment, fitness assessment, etc. Although systolic and diastolic blood pressure are illustrated in FIG. 4, it is understood that many other physiological metrics may be presented in accordance with embodiments of the present invention, such as heart rate, respiration rate and other breathing characteristics (e.g., breathing volume, peak breath velocity, breathing irregularities, and the like), cardiac output, blood pressure (e.g., systolic, diastolic, and mean pressure), blood oxygen, blood hydration status, and the like. Moreover, embodiments of the present invention may be used with physical activity metrics associated with the body or a part of the body as well, such as speed, distance traveled, physical position, physical location, user cadence (i.e., of an activity), rotational speed, acceleration, or the like. Such physiological and activity metrics may be sensed using various body-worn sensors that are well-known to those skilled in the art. Embodiments of the present invention are not limited to the presentation of blood pressure information and blood pressure sensor information.

Biometric information and sensor information can be presented in various ways in accordance with embodiments of the present invention. In general, at least one axis of a displayed graph is related to the sensor metric of interest and at least one other axis is related to a probability characteristic (i.e., such as a probability distribution or other function of probability) associated with that sensor metric. In the illustrated embodiment, of FIG. 4, blood pressure is plotted along the x-axis, and probability distribution is plotted along the y-axis. However, embodiments of the present invention are not limited to the illustrated presentation 40 of FIG. 4. For example, the x-axis and y-axis in FIG. 4 can be switched such that blood pressure (or another sensor metric) is plotted along the y-axis and the probability distribution is plotted along the x-axis. Moreover, alternative graphical representations may be used.

In the illustrated embodiment of FIG. 4, the presentation 40 shows the respective probability distributions for both systolic and diastolic pressure estimates centered around the estimated pressure data taken for one measurement. In this particular case, both the systolic and diastolic readings have come from a PPG-based sensor as described in U.S. Pat. Nos. 8,251,903, 8,647,270, and 8,700,111, the disclosures of which are incorporated herein by reference in their entireties. This would not necessarily imply that the estimated values presented would be the true values or the expected values of systolic or diastolic pressure for this instance in time, or that averaging multiple measurements with the subject at static blood pressure would result in the estimated values shown as being the expected value of the probability distribution for this instance in time. Rather, FIG. 4 presents the known statistical distributions of the blood pressure sensor centered around the estimated DP (diastolic pressure) and SP (systolic pressure) values from a single measurement, as though that single measurement were the mean or expected value of the distribution at a particular instance in time. The presentation 40 allows the user to have a basic understanding of the accuracy and/or precision of the measurement in view.

For example, the user will know that there is a 95% chance that the expected value (the true blood pressure value) is within about two (~2) standard deviations of the estimated number. An alternate methodology would be to only plot out the presentation 40 of FIG. 4 after multiple estimates of blood pressure had been generated, such that a true mean value can be calculated and plotted at the center of distribution. In practice, it may be best to generate this plot only after a statistically appropriate number of measurements have been generated. For example, a sensor characterized by a high correlation coefficient ($R^2$) with respect to a benchmark sensor may require fewer measurements for averaging to calculate and present the true center of the distribution to a user. However, it should be noted that taking multiple measurements to generate the true center of the distribution may require that the user be at a static blood pressure over the measurement collection period of time, and it may be impractical to assume that the subject's blood pressure would not change over that period of time.

In the illustrated embodiment of FIG. 3, it should be noted that the PPG sensor demonstrated≅0 mean bias with respect to the blood pressure cuff sensor, and so multiple measurements of both the PPG sensor and blood pressure cuff would be averaged to the same mean value. However, the cuff is clearly more precise (shows higher precision) than does the PPG sensor. It should be noted that for the sensor associated with the presentation 40 of FIG. 4, it is clear that the diastolic blood pressure estimate is more precise (i.e., has a tighter distribution) than is the systolic blood pressure estimate. However, in practice, because the range of healthy diastolic blood pressure values is smaller than for that of the systolic blood pressure, it may be more important to have a smaller $\sigma$ (a higher precision) for the diastolic readings than for the systolic readings.

Figure 5:
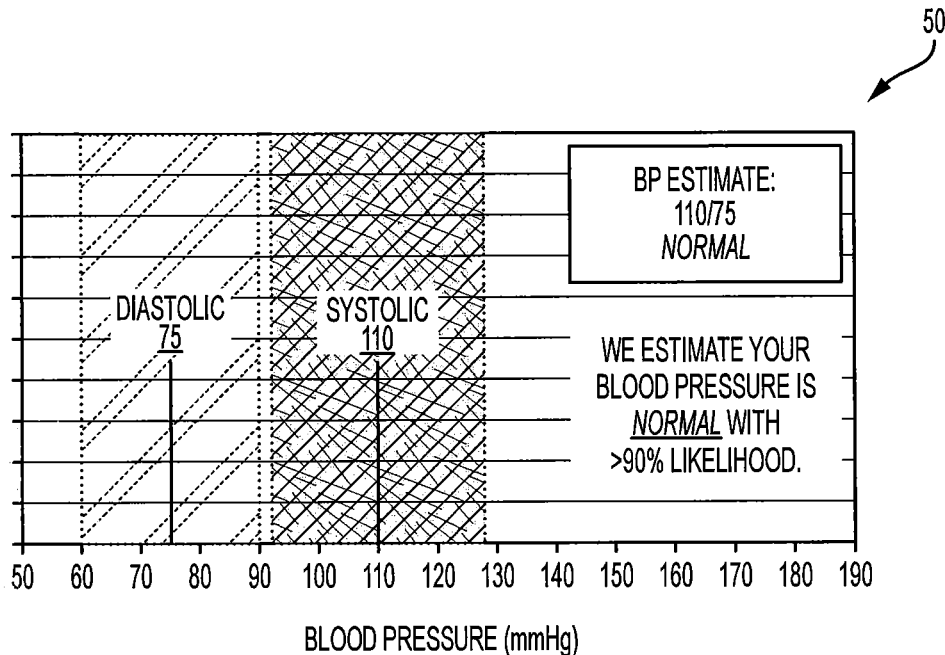

FIG. 5 illustrates an alternative presentation 50 to the presentation 40 of FIG. 4. The presentation 50 may be via a display of a mobile electronic device, for example, such as display 98 of client device 96 in FIG. 8. The presentation 50 of FIG. 5 illustrates how an application may present biometric information (in this case blood pressure information) to a user such that the user and/or someone monitoring the user can assess the accuracy or urgency of the biometric assessment (health assessment, fitness assessment, etc.), according to other embodiments of the present invention. The presentation 50 of FIG. 5 displays the same data used in FIG. 4, but the probability distributions are not shown. Rather, the 95% LOA are presented in shading such that the viewer understands the range of where the user's true blood pressure (or expected value) would likely be found, based on this single measurement. The information may be shown as a distribution, fading from the center (e.g., 75 mmHG) with color shading density representing the probability, e.g., shown as a Gaussian blur. Alternatively, the information may be shown as a range, without portending to a probability distribution, as shown for the systolic information in FIG. 5.

It should be noted that the statistical characteristics of a sensor may not always be Gaussian (normal) distributions, and in such case the presented probability distribution should reflect the true nature of that sensor. A variety of statistical distributions are well known by those skilled in the art, such as Poisson, Boltzmann, Bernoulli, and the like, and may be utilized in accordance with embodiments of the present invention.

Figure 6:
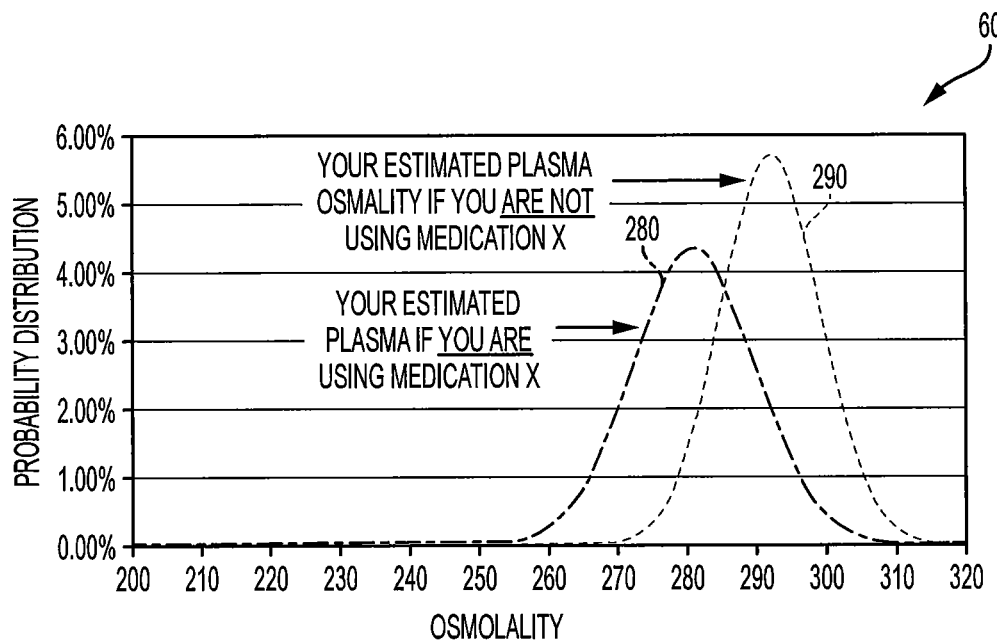

In some embodiments of the present invention, an estimation of a biometric parameter, based on sensor information collected by a mobile application, may be dependent on static or quasi-static biometric information. FIG. 6 illustrates a presentation 60 of hydration status information (such as blood hydration information), in terms of osmolality of a user, according to some embodiments of the present invention. The presentation 60 may be via a display of a mobile electronic device, for example, such as display 98 of client device 96 in FIG. 8. In the illustrated embodiment, it is known that the particular PPG-based osmolality sensor underestimates osmolality and reduces precision for users who are taking "medication X". In this particular case, since it is also known that the PPG-based osmolality sensor estimates osmolality with a lower accuracy and precision under the use of medication X, the mobile application is able to present this information to the viewer by processing data collected from the sensor. In this particular case, the information is presented as two separate plots for the cases where the user is using and is not using "medication X". It is important to emphasize that without this statistical data presented to the user or someone monitoring for the user, the ability to prescribe the appropriate therapy, treatment, or dosage of therapy/treatment "X" may be substantially hindered. For example, without such information, a medication "X" dosage designed to lower a physiological metric (heart rate, blood flow, blood hydration, blood oxygen, blood pressure, etc.) by Y % may be mistakenly applied to someone who should have that metric lowered by only a fraction of Y %.

Figure 7A:
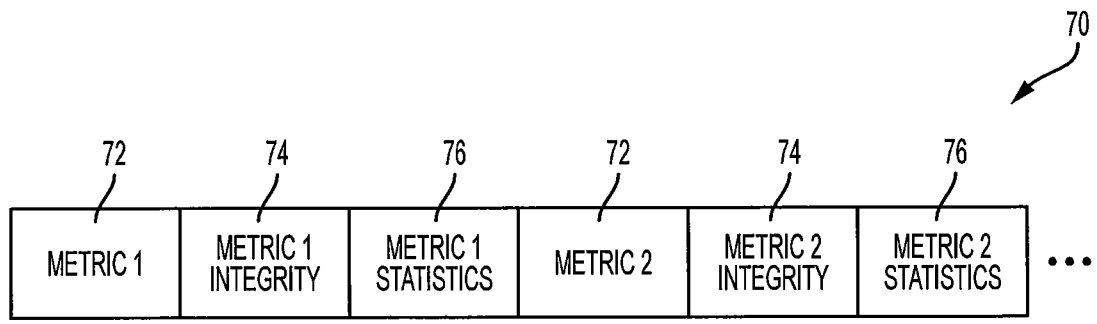
FIGS. 7A-7B illustrate serial data streams that include biometric information, information about the integrity of the biometric information, and other statistical information, according to some embodiments of the present invention.

According to some embodiments of the present invention, data may be presented to an app as a serial data stream containing not only the metrics measured by a sensor, but also information about the sensor data integrity and the sensor measurement statistics. For example, a serial data stream 70 is illustrated in FIG. 7A in which a metric 72, associated metric integrity 74, and metric statistic 76 are reported for each sensor measurement. Regular updates of metric statistics 76 may be important when statistics are changing dynamically. For example, if a sensor or associated processor detects an environmental condition (i.e., indoor or outdoor temperature condition, indoor or outdoor humidity condition, etc.), physical condition (i.e., age, blood perfusion, metabolic state, elevated biometric parameter, etc.), or physical activity (i.e., rest, exercise, shivering, shaking, controlled breathing, etc.) of the user that is known to change metric statistics, then these metric statistics may be changed dynamically in time with each sensor measurement to account for these changes in conditions. So as a particular example, if a wearable device comprises both an environmental sensor—in this case for measuring ambient temperature—and a physiological sensor—in this case a tympanic temperature sensor—and if it is known that the tympanic temperature sensor readings become less accurate with higher ambient temperature, then the reported metric statistics associated with tympanic temperature sensor may be updated to account for the lower accuracy.

Figure 7B:
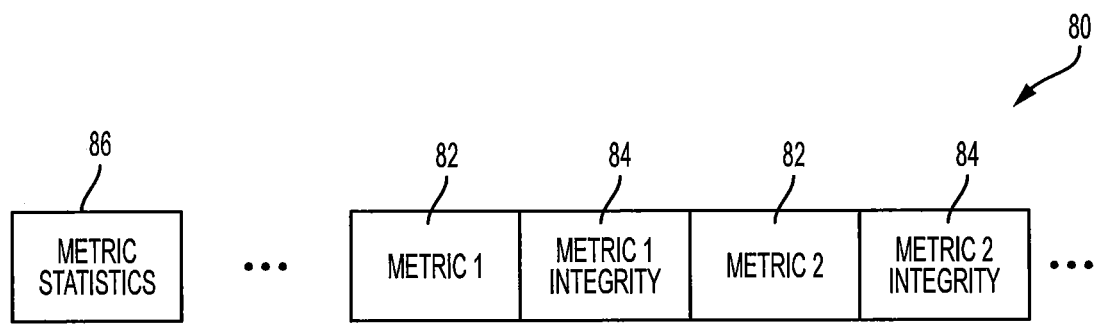

According to other embodiments as illustrated in FIG. 7B, a serial data stream 80 of metrics 82 and associated metric integrity 84 includes metric statistics 86 that are provided during the beginning of streaming data transmission only. This configuration may be useful when metric statistics are essentially static and do not change substantially with continued measurements.

Figure 8:
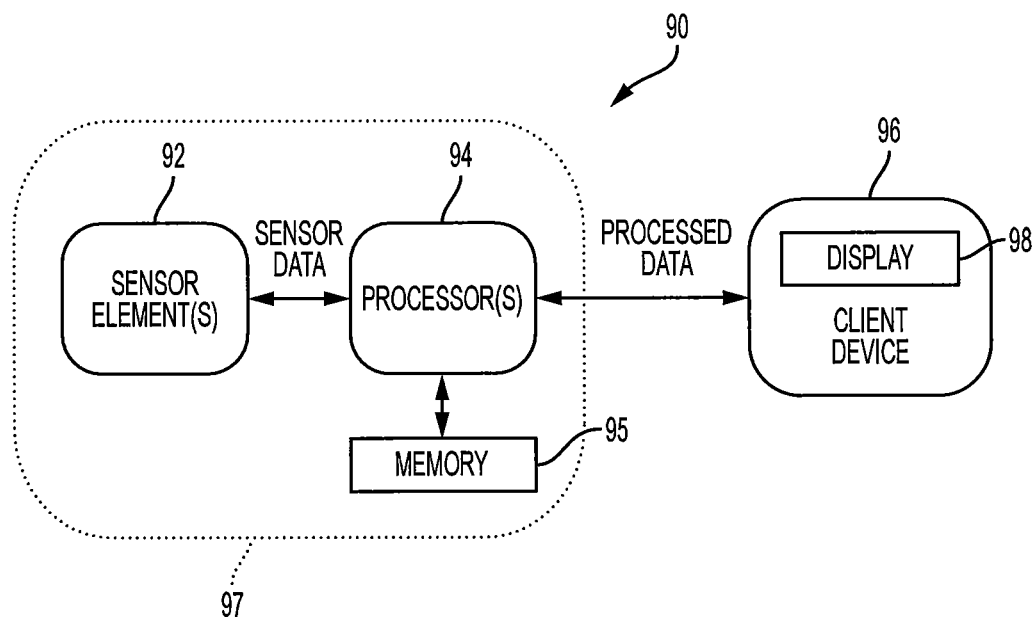
FIG. 8 is a block diagram of a system for implementing embodiments of the present invention.

In a specific example of the embodiment of FIG. 7B, consider a PPG sensor configured to sense blood flow information and body motion information. The PPG sensor in this example includes at least one optical emitter, at least one optical detector, and at least one motion sensor. Such a sensor is able to sense scattered light from the body of a subject, as well as body motion, and may also be configured to process that information, via a processor in communication with the sensor elements, into various metrics, such as heart rate, breathing rate, blood pressure, blood analyte levels, blood oxygenation levels, RRi, HRV, cadence, speed, jumping height, exercise frequency, and the like, as described in U.S. Pat. No. 8,700,111. A serial data stream from a PPG sensor, such as serial data stream 80 of FIG. 7B, may provide information not only about one or more of these metrics, but also about the data integrity of each metric and the statistics of each metric. In this way, a mobile app can present sensor data as shown in FIGS. 2-6 to a user, for example, via a display 98 of a client device 96 (FIG. 8). In the case of this particular PPG sensor, assuming it is enabled with active noise removal of noise artifacts from motion and the environment (as described in U.S. Pat. No. 8,888,701, which is incorporated herein by reference in its entirety), the sensor statistics may be essentially static throughout various conditions, and thus the metric statistics may be reported just once (represented by block 86) at the beginning of communication with a client device 96 (FIG. 8).

In a specific example of the embodiment of FIG. 7A, consider a bioimpedance sensor configured to sense impedance changes along the skin of a person during exercise. As the person exercises, the person's conditions may change, i.e., skin conductivity may change rapidly, due to sweat, skin temperature, and other factors. Each condition may affect the metric statistics. If the bioimpedance sensor, another sensor, or an associated processor is configured to measure such conditions, then the serial data stream, such as serial data stream 70 of FIG. 7A, may be modified to account for these dynamically changing statistics. As a specific example, an associated processor may process 1) skin sweat or skin hydration information from a skin sweat sensor or skin hydration sensor and 2) skin impedance from a bioimpedance sensor, such that the metric statistics of the bioimpedance sensor are updated based on the skin sweat or skin hydration values. The processing may comprise processing a function (linear or nonlinear) of these sensor inputs with metric statistics as the output. Alternatively, the processing may utilize a look-up table between the sensor inputs and the metric statistics. Other processing methodologies may be used, as well.

FIG. 8 illustrates a system 90 for implementing aspects of the present invention, and includes one or more sensor elements 92 configured to sense information (i.e., physiological and/or physical activity information about a subject; environmental information in a vicinity of the subject, etc.), one or more processors 94 configured to process sensor information and communicate processed information to a client device 96. The client device 96 is configured to receive processed information (such as data streams 70 or 80) and to make this information available for a person or device, for example via a display 98 of the client device 96. To understand and utilize the processed data from the sensor system 90, the client 96 may utilize a communication protocol, such as an application programming interface (API), associated with the sensor system 90. Utilizing an API may help the sensor system scale with multiple client(s) 96.

The arrows are drawn bi-directionally as the processor(s) 94 may communicate information to the sensor element(s) 92 (such as changing sensor polling, gain, actuation elements, etc.) and the client device 96 may send commands to reconfigure the processor(s) 94 (such as modifying processing algorithms or communication protocols). The dotted line 97 around the sensor element(s) 92 and processor(s) 94 represents the case of a "smart sensor", wherein the smart sensor 97 comprises both a sensor element 92, processor 94 and memory 95. For example, a smart photodetector for PPG monitoring may comprise a photodiode sensor element 92 and an associated processor 94 to actively bias the photodiode, control parameters of the associated optical emitters, control analog-to-digital conversion, actively remove motion artifacts and environmental artifacts via a noise reference and active filter (such as an adaptive filter or the like), or the like. However, embodiments of the present invention are not limited to an integrated smart sensor.

For example, a blood pressure sensor 92 may be combined with a perfusion sensor 92 to communicate with a processor 94. The processor may be configured to communicate a data stream to a client device 96. For example, a serial data stream 70 as shown in FIG. 7A may be communicated to a client device 96. Information from the perfusion sensor 92 may be processed by the processor 94 to update the metric statistics of the blood pressure sensor 92, as these may be changing dynamically in time. In some cases, the client device 96 may send a command to the processor 94 to change the processing characteristics. For example, if the client device 96 receives a message that the user is taking a medication, this may cause the processor 94 to change the metric statistics of the resulting data-stream such that the data communication is more accurate.

It should be noted that although serial configurations of data flow have been shown and may be more beneficial in practice, elements of the present invention may be used for parallel data transmission, where data from multiple sensors 92 is streamed in parallel rather than serially. In such case, the communication protocol (i.e., API) associated with the sensor system 90 may be configured for parallel data communication.

The system 90 of FIG. 8 may also be used for research or autonomous calibration purposes. For example, biometric sensor inputs may be processed to determine the metric integrity and metric statistics associated with the sensor 92. For example, the standard deviation of sensor measurements can be compared against a known relationship of a benchmark sensor, and then metric statistics can be updated for that sensor 92 based on these findings. Namely, there may be a relationship between the raw measurement statistics of a series of measurements (i.e., the standard deviation and/or mean of a plurality of sensor measurements) and the metric statistics (the standard deviation and/or mean of the differences between the sensor readings and benchmark readings), and the metric statistics may be updated based on changes in the measurement statistics.

Alternatively, a sensor 92 and an associated benchmark sensor may generate data for processing that may be used to judge the metric statistics of the sensor 92 with respect to the benchmark, and the metric statistics may be autonomously updated accordingly. In such a configuration, by processing sensor data and benchmark data over a period of time, a relationship may be learned between the metric integrity and metric statistics of a sensor 92. This information can then be updated in future processing of sensor data, such that dynamically changing metric integrity values may be processed into dynamically changing metric statistics values (FIG. 7A) in real-time.

For example, consider the processor(s) 94 of system 90 in which a first algorithm is used thereby to extract a signal from noise present in the sensor inputs and a second algorithm is used thereby to process this signal directly into a measurement to be reported. The first algorithm could measure the signal-to-noise (S/N) ratio of a metric and then express the S/N ratio as the metric integrity. In this example, a laboratory study may reveal that the sensor reported metric follows a normal distribution around the benchmark. This normal distribution could be reportable as metric statistics.

As another example, consider the case where a smart sensor 97 as described with respect to FIG. 8 (sensor element 92+processor 94+memory 95), is able to determine the number of valid measurements collected during a metric sampling period and is also able to relate a metric statistic/integrity that is dependent on the number of valid sample measurements, wherein the valid sample measurements comprise those sensor measurements characterized by a sufficiently high signal-to-noise (S/N) ratio. As a specific example, a PPG-based smart sensor 97 may be used to assess a metric, such as blood pressure, blood flow, blood hydration, blood analyte (bilirubin, hemoglobin, electrolyte, etc.) level, and the like. In such case, a plurality of PPG waveforms may be processed together to assess a single metric, but some waveforms may be noisy (due to motion noise or electrical noise, for example), and the metric statistics or metric integrity for that metric may be dependent on the number of valid waveforms used to process that metric. For example the standard deviation of the metric statistics may decrease (improve) with an increasing number of valid waveforms (for the metric sampling period) or an increasing ratio of valid waveforms to invalid waveforms. In such case, the algorithm on the processor used to process the metric may comprise a way of determining which PPG waveforms are valid, counting the number of valid waveforms, and comparing the valid number of waveforms with a relationship stored in memory 95 relating the number of valid waveforms to metric statistics and/or metric integrity. The processor 94 may then report the appropriate metric statistics and integrity to a client device 96 (based on the number of valid waveforms). As a specific example of determining whether a PPG waveform is valid, a processor 94 may process a waveform to determine the waveform's amplitude and/or slope, and if that waveform's amplitude and/or slope is outside of a desired range, the processor 94 may deem that waveform invalid.

Figure 9:
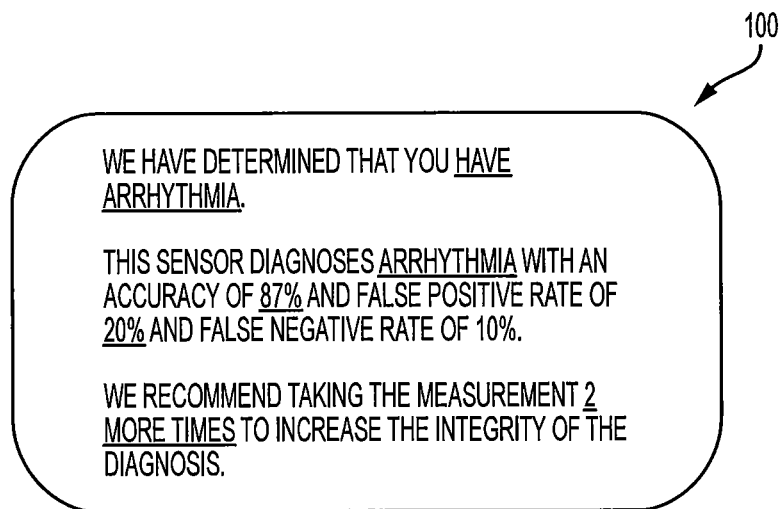
FIG. 9 illustrates a display of data to a user by a sensor system configured to generate a diagnostic (yes/no) assessment of a health condition, according to some embodiments of the present invention.

FIG. 9 illustrates a presentation 100 of data to a user or someone monitoring a user via a display 98 of a client device 96, such as a smartphone, by a sensor system 90 configured to generate a diagnostic (yes/no) assessment of a health condition, according to some embodiments of the present invention. In this example, sensitivity/specificity characteristics have been included in the data stream (e.g., data stream 70, 80 of FIGS. 7A-7B). As such, the application on the client device 96 can present not only the diagnosis (the metric) of arrhythmia but also the metric statistics associated with the arrhythmia diagnosis via the sensor system 90, such as the 87% accuracy, the 20% false positive rate, and the 10% false negative rate associated with the sensor system 90 diagnosing arrhythmia. This information can be useful in determining how to triage next steps for the user. In this case, a processor 94 associated with the sensor system 90 communicates next steps to the user or person monitoring the user (i.e., it communicates that the person should take the measurement 2 more times). This type of recommendation may be included in the data stream itself (e.g., data stream 70, 80 of FIGS. 7A-7B), characterized by the sensor properties themselves, or may be processed by a processor, such as a processor associated with the client device 96, via an algorithm configured to process metric statistics information into a recommendation. In this example, following the third test, the user or person monitoring the user may be prompted with an overall assessment or further next steps. The display methodology of FIG. 9 can be extremely useful in facilitating an autonomous diagnosis while also preventing overreactions (or underreactions) from false positives and false negatives by providing statistical context to the user or someone monitoring the user.

Though many examples of the invention described herein have referenced biometric sensors for physiological monitoring, it should be noted that voice sensors may also be used, according to embodiments of the present invention. For example, a voice sensor may be known to have a certain statistical probability of identifying voice information—such as identifying words, phrases, a person's biometric identification, and the like. Thus, a voice sensor 92 in communication with a client device 96 may send a serial data stream of information comprising the voice ID information (i.e., the metric), the probability that the voice ID information is correct (i.e., the metric statistic), and the quality of the voice information itself (i.e., the metric integrity). The client device 96 may then determine, based on all of this information, whether or not to execute the voice information. As a specific example, the client device 96 may collect serial data stream information from the voice sensor 92 for the purpose of executing the voice command "turn on" (i.e., the "sensor metric" is "turn on"). But the client device 96 may also have information that the decibel level was very low (i.e., the "metric integrity" was very low) and that the particular voice sensor 92 has a command transcription error ("metric statistic" error) of 25%. Thus, the processor in the client device 96 may process all this information to determine that the voice command "turn on" should not be executed; the client device 96 may then visually show the user via display 98 that the command "turn on" may have been requested by the voice sensor 92 but was not executed by the client device 96 due to unsatisfactory sensor integrity and sensor statistics.

According to other embodiments of the present invention, a communications protocol that is capable of transferring information from a physiological sensor 92 to a client device 96 is provided. In this protocol, events described below may occur as appropriate for the communications medium. For instance, event instances can be polled from a sensor 92 by a client device 96, or sent at regular intervals (e.g., set by the sensor 92 or by the client device 96 or by convention), or sent asynchronously as measurement data becomes available or changes.

Figure 10:
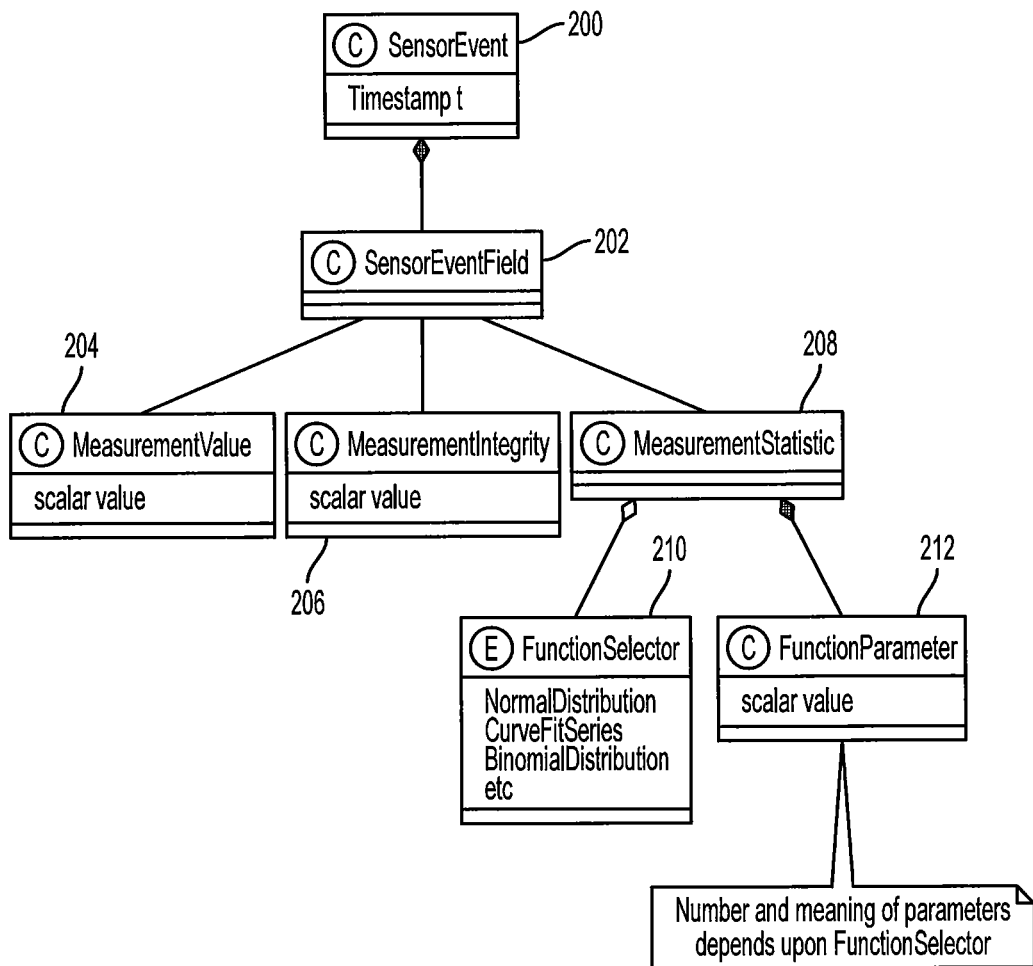
FIG. 10 illustrates a communication protocol presented as a series of SensorEvents, according to some embodiments of the present invention.

According to some embodiments of the present invention, the communication protocol is presented as a series of SensorEvents, such as that shown in FIG. 10. A SensorEvent 200 may contain a Timestamp and one or more SensorEventField 202. Each SensorEventField 202 is one of the following: a MeasurementValue (one or more scalar numbers, depending on sensor) 204, a MeasurementIntegrity (scalar) 206, or a MeasurementStatistic 208 (described below). It should be understood that variations of FIG. 10 are permissible under embodiments of the present invention, and FIG. 10 represents just one potential embodiment.

For sensors 92 where a laboratory study determines that the measurement statistics do not change (FIG. 7B), a SensorEvent 200 containing one or more MeasurementStatistic 208 can be sent upon start up (i.e., sensor start up), upon connection, periodically, or even with every MeasurementValue 204. Other sensors 92 could take advantage of the protocol supporting all fields changing dynamically and being updated per SensorEvent 200. The MeasurementStatistic 208, described below, is rich enough to describe or approximate the statistical complexity of biological and natural processes, yet compact enough to be practical for transmission by battery powered devices.

The MeasurementStatistic 208 may consist of the following: FunctionSelector 210, and one or more FunctionParameters 212. The FunctionSelector 210 is a selection from statistical distribution functions, some of which may be well-known functions, or from a special value indicating a series of points for curve fitting (to allow even greater flexibility). Non-limiting examples include NormalDistribution (Gaussian), CurveFitSeries, ROC (Receiver Operating Characteristic) Curves, and BinomialDistribution. However, it is understood that other statistical distribution curves may be utilized in accordance with embodiments of the present invention.

Table 1 below illustrates each appropriate FunctionParameter 212 for each FunctionSelector 210.

TABLE 1

| FunctionSelector | FunctionParameters |
| --- | --- |
| NormalDistribution | $\mu$, $\sigma$ |
| CurveFitSeries | Num point pairs (n), $x_0$, $p_0$, $x_1$, $p_1$, ... $x_n$, $p_n$ |
| BinomialDistribution | N, p |

An advantage of embodiments of the present invention is that virtually any sensor of a given metric (e.g., physiological, environmental, etc.) can be used by a client device to generate an assessment for a subject or group of subjects, with contextual statistical information as a guide. For example, if heart rate readings are utilized by a client device to estimate caloric metabolism, the accuracy of this model, based on heart rate, can be presented to the user in context with the statistics/integrity of the heart rate values. Moreover, if ECG information is utilized by a client device to assess a cardiac condition (such as a heart attack, arrhythmia, atrial fibrillation, and the like), then the likelihood that that condition exists (or does not exist) can be presented to the subject(s) or someone monitoring the subject(s) in context of the statistics/integrity of the ECG values. This is particularly valuable for a marketplace where there may be numerous vendors offering the same types of sensors, but with each sensor having different metric integrity and/or metric statistics characteristics, to be used with client devices in generating multiparametric physiological assessments. Indeed, the invention promotes accuracy and precision in a competitive marketplace, because competing sensors can be differentiated in the marketplace based on the accuracy and precision of their measurements as determined by prior clinical studies for that particular sensor, where the prior clinical studies have determined the metric integrity and/or metric statistics for that sensor. In some use cases, the greatest accuracy and precision may be critical. But in others, more cost-effective sensors, which may not exhibit the ideal accuracy and/or precision, may be "good enough", depending the on the diagnoses made and the expense or risks of the resulting therapy. Because the metric statistics and metric integrity of sensor data required to diagnose and treat various health conditions is often known way in advance of a medical product launch, in part due to regulatory requirements, the proposed invention may provide full visibility to the marketplace to pick and choose "good enough" sensors based on price. Thus, the invention supports positive market forces to drive down costs and also to promote safety in medical products. Additionally, with embodiments of the present invention, the client software for each sensor may not need to be rewritten for each sensor offered by the vendors, as the client assessments can always be generated and reviewed in context of sensor statistics.

For some sensor metrics and sensor modalities, the metric statistic associated with a sensor system 90 may be highly personalized to the user, such that an impersonal (generic) metric statistic may be of substantially less value. Namely, the same sensor system 90 used on 2 different subjects may not have the same metric statistic for each subject, and thus the expected accuracy of the sensor metric for one person may be different than that for another person. In such case, a subject-specific metric statistic may be highly valuable, wherein the metric statistic information may be processed for each subject at the time of measurement, based on metric features for the subject. As a specific embodiment, the sensor element(s) 92 may send data to a processor (such as the processor 94 or other processor in the sensor system 90) for the purpose of generating a metric to be presented on a client device 96. The processor 94 may then process the sensor data to generate metric features to be used in generating a sensor metric for the user—for example, via a machine learning algorithm with metric features as the inputs and a sensor metric as the output—and to additionally process the metric features to determine the subject-specific metric statistic associated with the desired sensor metric. Thus, the client device 96 may receive the sensor metric as well as the subject-specific metric statistic for the given measurement.

Subject-specific metric statistics may be especially useful in measurements where the meta data for a subject has a substantial impact on the accuracy of the sensor metric estimation. This can be especially important for the case where the sensor metric is generated by processing sensor data via an algorithm developed via machine learning. A general embodiment of the invention is presented in FIG. 11. In this embodiment, input data (including sensor data and subject meta data) is collected from a subject via the sensor system 90 (Block 300). Subject meta data can be obtained in various ways. In some cases, subject meta data may be input by the subject or a third party; in o other cases, subject meta data may be obtained from sensor data, such as via a video imaging device, a camera, an audio sensing device, or the like.

The input data is then processed to determine metric features (Block 302). Metric features may include the various features of waveforms, such as PPG waveforms, such as, but not limited to, RR-interval (i.e., beat-to-beat interval) features, rising slope(s), falling slope(s), integral of the waveform(s), spectral features of the waveforms, peak amplitudes of the waveforms, features generated by mathematical transforms of the waveforms (such as wavelet transforms, Fourier transforms, the Teager-Kaiser energy operator, chirplet transforms, noiselet transforms, and the like), waveform amplitude(s), waveform skews, auto-correlational features, and the like. In addition, metric features may include subject meta data, such as subject age, height, weight, medication usage, gender, ethnicity, etc. These metric features are then processed to determine a subject-specific metric statistic (as well as the sensor metric itself) (Block 304). The sensor metric and subject-specific metric statistic are then presented via a client device, e.g., via a display of a client device, for example as illustrated in FIGS. 2-6 (Block 306). The processing steps may be executed by at least one processor 94 in the sensor system 90. (It should be noted that the metric must also of course be processed in order to be presented. However, this step may occur at any point once the metric features are determined.) The processing of metric features to determine a subject-specific metric statistic may employ data clustering techniques—such as k-means, Gaussian mixture models or the like—to generate feature clusters. Data clustering techniques which may be utilized in accordance with embodiments of the present invention are disclosed in, for example, Mathematics for Machine Learning, by Marc Peter Deisenroth, et al., 2019, Cambridge University Press, https://mml-book.com.

It has been found through experimentation by the inventors that these clusters are often associated with notably higher or lower accuracy for the metric statistics. Thus, a collection of metric features that are determined to be part of a low- or high-accuracy feature cluster may then be qualified as being associated with low- or high-accuracy metric predictions, respectively, and the reported subject-specific metric statistic will reflect such. For example, the metric features may be determined to be most associated with a feature cluster associated with a metric statistic having a known mean ±STDEV (standard deviation) error. Thus the subject-specific metric statistic for the desired sensor metric may be presented as the known mean±STDEV error. Alternatively, the subject-specific metric statistic may be presented as a qualification of the known mean ±STDEV error, such as a "good enough" indication for the accuracy of the sensor metric. In an embedded solution, this invention may employ memory (such as electronic memory 95) to store information relating known feature clusters to known accuracy values. Thus, if the processor 94 determines that the metric features belong to a low-accuracy cluster, the metric statistic may then be reported as either the known accuracy (for that cluster); alternatively, the metric statistic may be reported as a qualification (such as "good enough" or "not good enough").

Figure 11:
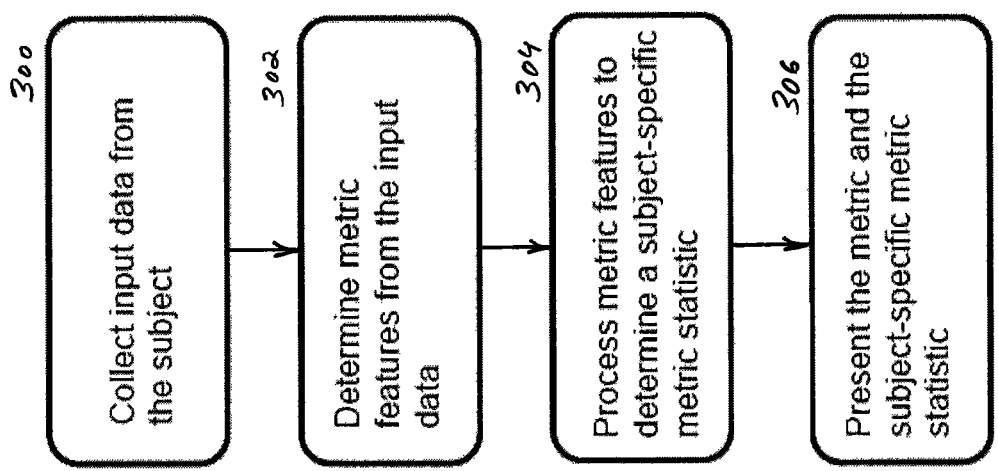
FIGS. 11-13 are flow diagrams illustrating methods of producing and displaying subject-specific metric statistics, according to various embodiments of the present invention.
Figure 12:
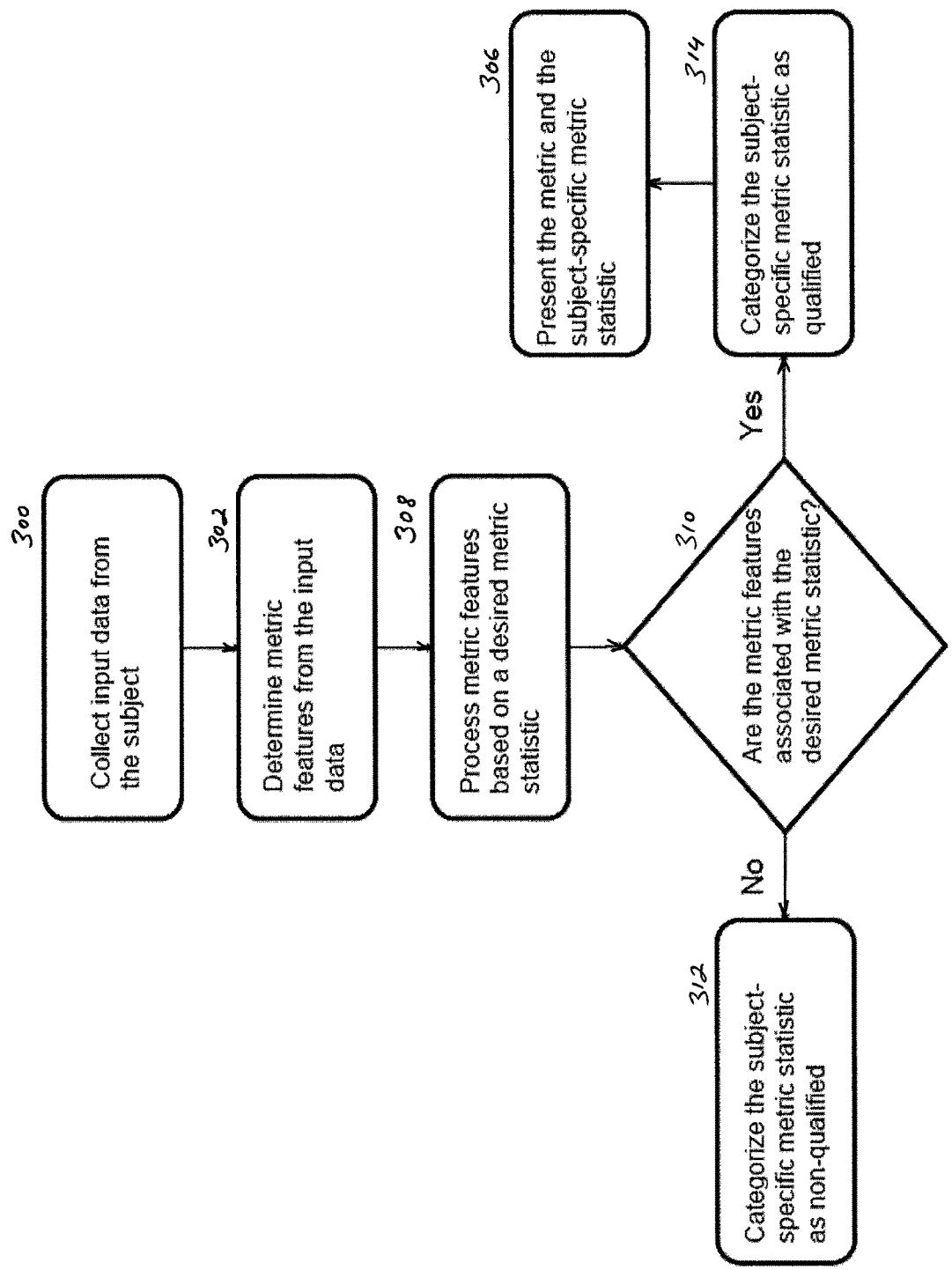

A specific embodiment of FIG. 11 is presented in FIG. 12. In this embodiment, the processing of metric features to determine a subject-specific metric statistic may comprise processing metric features based on a desired metric statistic (Block 308). For example, it may be known that a desired mean ±STDEV error for the metric is less than or equal to 5±8. The metric features may then be processed with respect to this desired ≤5±8 metric statistic to determine if the metric can possibly meet the desired error criteria (Block 310). (As with the prior example, the processing may employ clustering or other such processing techniques.) If "yes", then the reported subject-specific metric statistic may be categorized as "qualified" (Block 314). If "no", then the reported subject-specific metric statistic may be deemed as "non-qualified" (Block 312). In either case, the reported subject-specific metric statistic and associated metric may be presented via a client device (Block 306).

Figure 13:
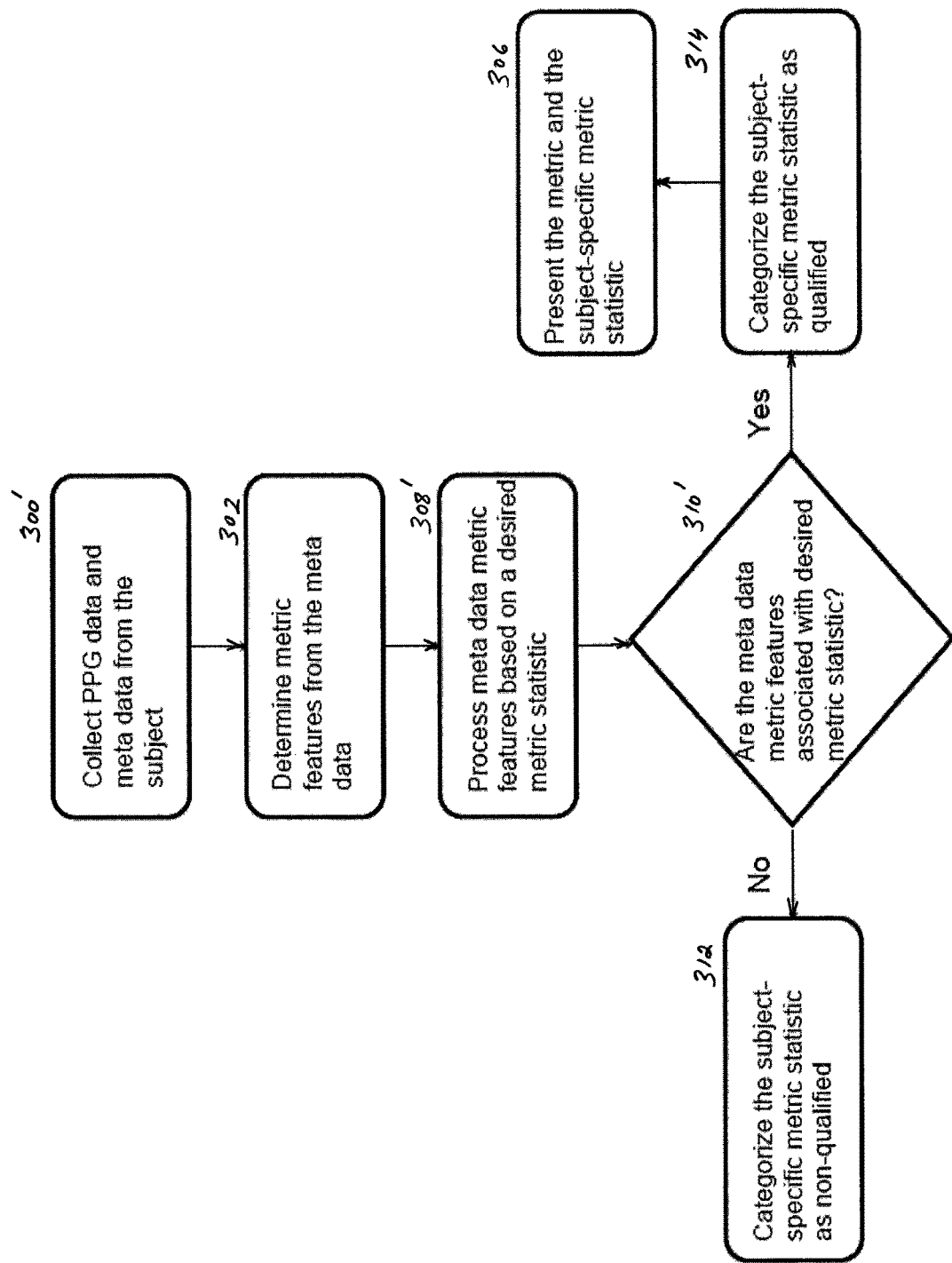

A specific embodiment of FIG. 12 is presented in FIG. 13. This embodiment takes advantage of subject meta data as means of qualifying the accuracy of a sensor metric—in this case subject blood pressure. In this embodiment, the sensor input data comprises both PPG data and meta data from the subject (such as from a PPG sensor and a meta data input device), where the meta data may comprise subject-specific static biometrics (such as subject height, weight, BMI, age, gender, ethnicity, skin tone, medication usage, and the like) (Block 300'). The algorithm for generating the subject blood pressure metric comprises a machine learning algorithm that processes both PPG features and meta data features as inputs to generate an output estimate of subject blood pressure with a similar accuracy to a medical grade blood pressure cuff. Thus, the targeted metric statistic comprises an error ≤5±8 mmHg (consistent with the ISO-81060:2 standard) with respect to the manual blood pressure cuff. However, experiments by the inventors have shown that some clusters of meta data features are associated with sensor readings that are likely to yield less accurate metric statistics than other clusters. Thus, in this specific embodiment, processing is executed to determine the subject meta data metric features (Block 302) and to determine if they belong to a feature cluster that is associated with the targeted metric statistic (an error ≤5±8 mmHg), such that the subject-specific metric statistic will be expected to meet this target.

Following the determination that the targeted metric statistic is likely to be achieved (Block 310'), the subject-specific metric statistic may be categorized as "qualified" (Block 314). In contrast, if it is determined that the target metric statistic is unlikely to be achieved (i.e., that the subject meta data metric features belong to a feature cluster that is not associated with the targeted metric statistic), then the metric statistic may be categorized as "non-qualified" (Block 312).

This invention has at least two key benefits. The first benefit is that it enables a much higher certainty in the accuracy of the sensor metric determination (since subject-specific data is utilized in the processing). The second benefit is that it enables power savings, as PPG feature processing is not required for measurements where it is expected (through processing the meta data) that the sensor metric determination will not fall within the targeted metric statistic(s). The second benefit is further supported by the fact that PPG feature processing is substantially more processing intensive than meta data processing, as the meta data features may simply be the input meta data itself (i.e., the meta data entered by the subject may be the features used), whereas PPG feature processing may require computationally intensive data transforms and high-sample-rate processing.

Example embodiments are described herein with reference to block diagrams and flowchart illustrations. It is understood that a block of the block diagrams and flowchart illustrations, and combinations of blocks in the block diagrams and flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor circuit and/or other programmable data processing apparatus, transform and control transistors, values stored in memory locations, and other hardware components within such circuitry to implement the functions/acts specified in the block diagrams and flowchart block or blocks, and thereby create means (functionality) and/or structure for implementing the functions/acts specified in the block diagrams and flowchart blocks.

These computer program instructions may also be stored in a tangible computer-readable medium that can direct a client device or other programmable data processing apparatus to function in a particular manner, such that the instructions stored in the computer-readable medium produce an article of manufacture including instructions which implement the functions/acts specified in the block diagrams and flowchart blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-eRay).

The computer program instructions may also be loaded onto a client device and/or other programmable data processing apparatus to cause a series of operational steps to be performed on the client device and/or other programmable apparatus to produce a computer-implemented process such that the instructions which execute on the client device or other programmable apparatus provide steps for implementing the functions/acts specified in the block diagrams and flowchart blocks. Accordingly, embodiments of the present invention may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and block diagrams may be separated into multiple blocks and/or the functionality of two or more blocks of the flowcharts and block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A sensor system, comprising:
at least one sensor configured to sense physiological data from a subject; and
at least one signal processor configured to:
receive the physiological data from the at least one sensor;
receive subject meta data;
process the subject meta data to determine a plurality of metric features, wherein each of the plurality of metric features is a feature of the subject meta data that is functionally related to generation of at least one sensor metric from the physiological data;
process the plurality of metric features to determine at least one subject-specific metric statistic for the subject, wherein the subject-specific metric statistic comprises information related to a performance, accuracy, sensitivity, and/or selectivity of the at least one sensor metric;
process the physiological data to generate the at least one sensor metric; and
present the at least one sensor metric for display via a display.

2. The sensor system of claim 1, wherein the at least one signal processor is configured to receive the subject meta data as input from the subject or a third party.

3. The sensor system of claim 1, wherein the at least one signal processor is configured to receive the subject meta data from a video sensing device and/or an audio sensing device.

4. The sensor system of claim 1, wherein the subject meta data comprises one or more of the following: subject age, subject weight, subject height, subject medication usage, subject gender, subject ethnicity, subject skin tone, subject body mass index (BMI).

5. The sensor system of claim 1, wherein the at least one sensor is a photoplethysmography (PPG) sensor, and wherein the physiological data comprises PPG data.

6. The sensor system of claim 1, wherein the at least one sensor metric comprises a subject blood pressure reading, and wherein the at least one subject-specific metric statistic comprises an accuracy likelihood for the blood pressure reading.

7. The sensor system of claim 6, wherein the accuracy likelihood comprises a likelihood that the blood pressure reading accuracy is ≤5±8 mmHg with respect to a reading from a manual blood pressure cuff.

8. The sensor system of claim 1, wherein the display is a display of a mobile communication device.

9. The sensor system of claim 1, wherein the at least one signal processor is further configured to present the at least one subject-specific metric statistic for display via the display.

10. A sensor system, comprising:
at least one sensor configured to sense physiological data from a subject; and
at least one signal processor configured to:
receive the physiological data from the at least one sensor;
receive subject meta data;
process the subject meta data to determine a plurality of metric features;
process the physiological data to determine a sensor metric, wherein each of the plurality of metric features is a feature of the subject meta data that is functionally related to generation of at least one sensor metric from the physiological data;
process the metric features to determine at least one subject-specific metric statistic for the subject, wherein the subject-specific metric statistic comprises information related to a performance, accuracy, sensitivity, and/or selectivity of the at least one sensor metric, to determine whether the at least one subject-specific metric statistic is associated with a targeted metric statistic for the sensor metric, and to determine a qualification associated with the sensor metric.

11. The sensor system of claim 10, wherein the sensor metric comprises a subject blood pressure reading and wherein the qualification comprises an accuracy likelihood for the blood pressure reading.

12. The sensor system of claim 11, wherein the accuracy likelihood comprises the likelihood that the blood pressure reading accuracy is ≤5±8 mmHg with respect to a reading from a manual blood pressure cuff.

13. The sensor system of claim 10, wherein the at least one processor is configured to receive the subject meta data as input from the subject or a third party.

14. The sensor system of claim 10, wherein the at least one processor is configured to receive the subject meta data from a video sensing device and/or an audio sensing device.

15. The sensor system of claim 10, wherein the subject meta data comprises one or more of the following: subject age, subject weight, subject height, subject medication usage, subject gender, subject ethnicity, subject skin tone, subject body mass index (BMI).

16. The sensor system of claim 10, wherein the at least one sensor is a photoplethysmography (PPG) sensor, and wherein the physiological data comprises PPG data.

17. A method, comprising:
collecting physiological data and meta data from a subject via a sensor system, wherein the sensor system comprises at least one sensor element, at least one signal processor, and memory in communication with the at least one signal processor;
processing the subject meta data via the at least one signal processor to determine a plurality of metric features, wherein each of the plurality of metric features is a feature of the subject meta data that is functionally related to generation of at least one sensor metric from the physiological data;
processing the plurality of metric features via the at least one signal processor to determine at least one subject-specific metric statistic for the subject, wherein the subject-specific metric statistic comprises information related to a performance, accuracy, sensitivity, and/or selectivity of the at least one sensor metric;
processing the physiological data via the at least one signal processor to generate at least one sensor metric; and
presenting the at least one sensor metric for display via a display.

18. The method of claim 17, wherein collecting the meta data from the subject comprises receiving the meta data as input from the subject or a third party.

19. The method of claim 17, wherein collecting the meta data from the subject comprises receiving the meta data from a video sensing device and/or an audio sensing device.

20. The method of claim 17, wherein collecting the meta data from the subject comprises determining the meta data from the physiological data.

21. The method of claim 17, wherein the subject meta data comprises one or more of the following: subject age, subject weight, subject height, subject medication usage, subject gender, subject ethnicity, subject skin tone, subject body mass index (BMI).

22. The method of claim 17, wherein the at least one sensor is a photoplethysmography (PPG) sensor, and wherein the physiological data comprises PPG data.

23. The method of claim 17, wherein the at least one sensor metric comprises a subject blood pressure reading, and wherein the at least one subject-specific metric statistic comprises an accuracy likelihood for the blood pressure reading.

24. The method of claim 23, wherein the accuracy likelihood comprises a likelihood that the blood pressure reading accuracy is ≤5±8 mmHg with respect to a reading from a manual blood pressure cuff.

25. The method of claim 17, further comprising presenting the at least one subject-specific metric statistic via the display.

26. The method of claim 17, wherein the display is a display of a mobile communication device.

27. A method, comprising:
collecting physiological data and meta data from a subject via a sensor system, wherein the sensor system comprises at least one sensor element, at least one signal processor, and memory in communication with the at least one signal processor;
processing the subject meta data via the at least one signal processor to determine a plurality of metric features, wherein each of the plurality of metric features is a feature of the subject meta data that is functionally related to generation of at least one sensor metric from the physiological data;
processing the physiological data via the at least one signal processor to determine a sensor metric; and
processing the plurality of metric features via the at least one signal processor to determine at least one subject-specific metric statistic for the subject, wherein the subject-specific metric statistic comprises information related to a performance, accuracy, sensitivity, and/or selectivity of the at least one sensor metric, to determine whether the at least one subject-specific metric statistic is associated with a targeted metric statistic for the sensor metric, and to determine a qualification associated with the sensor metric.

28. The method of claim 27, wherein the sensor metric comprises a subject blood pressure reading and wherein the qualification comprises an accuracy likelihood for the blood pressure reading.

29. The method of claim 28, wherein the accuracy likelihood comprises the likelihood that the blood pressure reading accuracy is ≤5±8 mmHg with respect to a reading from a manual blood pressure cuff.

30. The method of claim 27, wherein the sensor system is configured to receive the subject meta data as input from the subject or a third party.

31. The method of claim 27, wherein the sensor system is configured to receive the subject meta data from a video sensing device and/or an audio sensing device.

32. The method of claim 27, wherein the subject meta data comprises one or more of the following: subject age, subject weight, subject height, subject medication usage, subject gender, subject ethnicity, subject skin tone, subject body mass index (BMI).

33. The method of claim 27, wherein the at least one sensor is a photoplethysmography (PPG) sensor, and wherein the physiological data comprises PPG data.

* * * * *

UNITED STATES PATENT AND TRADEMARK OFFICE
CERTIFICATE OF CORRECTION

PATENT NO. : 11,617,545 B2  
APPLICATION NO. : 17/394565  
DATED : April 4, 2023  
INVENTOR(S) : LeBoeuf et al.

Page 1 of 1

It is certified that error appears in the above-identified patent and that said Letters Patent is hereby corrected as shown below:

In the Specification

Column 10, Line 20: Please correct "6)" to read --σ)--

In the Claims

Column 23, Line 47, Claim 10: Please correct "process the metric" to read --process the plurality of metric--

Signed and Sealed this  
Fourth Day of July, 2023

Katherine Kelly Vidal  
*Director of the United States Patent and Trademark Office*